(12) United States Patent
Walthall, Jr.

(10) Patent No.: US 9,511,119 B2
(45) Date of Patent: Dec. 6, 2016

(54) PREPARATIONS CONTAINING HEPATOCYTE GROWTH FACTOR AND HYALURONIC ACID AND METHODS OF MAKING AND USING SAME

(71) Applicant: NuTech Spine, Inc., Birmingham, AL (US)

(72) Inventor: Howard P. Walthall, Jr., Birmingham, AL (US)

(73) Assignee: NuTech Spine, Inc., Birmingham, AL (US)

( * ) Notice: Subject to any disclaimer, the term of this patent is extended or adjusted under 35 U.S.C. 154(b) by 0 days.

(21) Appl. No.: 14/211,929

(22) Filed: Mar. 14, 2014

(65) Prior Publication Data

US 2014/0274899 A1    Sep. 18, 2014

Related U.S. Application Data

(60) Provisional application No. 61/790,075, filed on Mar. 15, 2013.

(51) Int. Cl.

| | | |
|---|---|---|
| *A61K 38/18* | (2006.01) | |
| *A61K 47/36* | (2006.01) | |
| *A61F 2/00* | (2006.01) | |
| *A61F 13/00* | (2006.01) | |
| *A61L 27/20* | (2006.01) | |
| *A61K 8/64* | (2006.01) | |
| *A61K 8/73* | (2006.01) | |
| *A61Q 19/08* | (2006.01) | |

(52) U.S. Cl.
CPC ............. *A61K 38/1833* (2013.01); *A61K 8/64* (2013.01); *A61K 8/735* (2013.01); *A61L 27/20* (2013.01); *A61Q 19/08* (2013.01); *A61K 2800/91* (2013.01); *A61L 2300/414* (2013.01); *A61L 2400/06* (2013.01); *A61L 2430/02* (2013.01); *A61L 2430/06* (2013.01); *A61L 2430/10* (2013.01); *A61L 2430/24* (2013.01); *A61L 2430/34* (2013.01); *A61L 2430/38* (2013.01)

(58) Field of Classification Search
None
See application file for complete search history.

(56) References Cited

U.S. PATENT DOCUMENTS

| | | | |
|---|---|---|---|
| 4,544,516 A | 10/1985 | Hughes et al. | |
| 5,399,351 A | 3/1995 | Leshchiner et al. | |
| 5,486,359 A | 1/1996 | Caplan et al. | |
| 5,612,028 A | 3/1997 | Sackier et al. | |
| 6,152,142 A | 11/2000 | Tseng | |
| 6,162,908 A * | 12/2000 | Itano et al. | 536/23.2 |
| 6,326,019 B1 | 12/2001 | Tseng | |
| 6,355,239 B1 | 3/2002 | Bruder et al. | |
| 7,824,711 B2 | 11/2010 | Kizer | |
| 8,093,365 B2 * | 1/2012 | Wisniewski | A61K 47/4823 530/350 |
| 8,420,601 B2 * | 4/2013 | Wisniewski | A61K 47/4823 514/17.1 |
| 2004/0161419 A1 | 8/2004 | Strom et al. | |
| 2004/0181240 A1 | 9/2004 | Tseng et al. | |
| 2007/0071740 A1 * | 3/2007 | Tseng | A61K 35/48 424/94.1 |
| 2007/0093905 A1 * | 4/2007 | O'Neil et al. | 623/17.16 |
| 2007/0218039 A1 | 9/2007 | Devi et al. | |
| 2007/0231401 A1 | 10/2007 | Tseng et al. | |
| 2008/0102135 A1 | 5/2008 | Ollivier | |
| 2010/0168869 A1 * | 7/2010 | Long et al. | 623/23.72 |
| 2011/0038921 A1 * | 2/2011 | Wen et al. | 424/445 |
| 2012/0100185 A1 * | 4/2012 | Wen et al. | 424/400 |

OTHER PUBLICATIONS

Ruvinov, Emil et al., The effects of controlled HGF delivery from an affinity-binding alginate biomaterial on angiogenesis and blood perfusion in a hindlimb ishemia model. Biomaterial 31 (2010) pp. 4573-4582.
Boo, Lily et al., A Preliminary Study of Human Amniotic Membrane as a Potential Chondrocyte Carrier. Malaysian Orthopaedic Journal 2009, vol. 3 No. 2.
Vishwakarma, G.K., Amniotic Arthroplasty for Tuberculosis of the Hip, The Journal of Bone and Joint Surgery. vol. 68 B. No. 1, Jan. 1986.
Moriya, Takuro et al., Evaluation of reparative cartilage after autologous chondrocyte implantation for osteochondritis dissecans: histology, biochemistry and MR imaging. Journal of Orthopaedic SC, 2007.
Zhou, Shuanhu et al., Demineralized bone promotes chondrocyte or osteoblast differentiation of human marrow stromal cells cultured in collagen sponges, National Institute of Health Author of Manuscript. Cell Tissue Bank, 2005.
Hildner, F. et al., State of the Art and future perspectives of articular cartilage regeneration: a focus on adipose-derived stem cells and platelet-derived products. Journal of Tissue Engineering and Regenerative Medicine, 2011.
Krishnamurithy, G. et al., Human amniotic membrane as a chondrocyte carrier vehicle/substrate: In vitro study. Journal of Biomedical Materials Research A. vol. 99A, Issue 3, 2011.
Jin, Cheng Zhe et al., Human Amniotic Membrane as a Delivery Matrix for Articular Cartilage Repair. Tissue Engineering, vol. 13, No. 7, 2007.
Lindenmair, Andrea et al., Osteogenic differentiation of intact human membrane. Biomaterials 31 (2010) 8659-8665.
Diaz-Prado, Silvia et al., Potential use of human amniotic membrane as a scaffold in human articular cartilage repair. Cell Tissue Bank (2010) 11: 183-195.

(Continued)

*Primary Examiner* — Marianne P Allen
(74) *Attorney, Agent, or Firm* — C. Brandon Browning; Maynard, Cooper & Gale, PC

(57) ABSTRACT

Preparations containing hepatocyte growth factor (HGF) and hyaluronic acid (HA) and methods of making and using same. The HGF and HA preparations can be prepared together in solution as an injectable fluid without gelatinization, or impregnated within a porous hydrophilic matrix material with, or without, cross-linking of the HA with the matrix material. The preparations can be used as a dermal filler or to generate and promote healing of cartilage, vertebral discs, connective tissues such as tendons and ligaments and bone in vivo.

13 Claims, No Drawings

(56) References Cited

OTHER PUBLICATIONS

Wilshaw, Stacy-Paul et al., Production of an Acellular Amniotic Membrane Matrix for Use in Tissue Engineering. Tissue Engineering vol. 12, No. 8. 2006.

Niknejad, Hassan et al., Properties of the Amniotic Membrane for Potential Use in Tissue Engineering. European Cells and Materials. vol. 15 2008 (pp. 88-99).

Kanthan, S.R. et al., The Different Preparations of Human Amniotic Membrane (HAM) as a Potential Cell Carrier for Condrocytes. European Cells and Materials vol. 20. Suppl. 2, 2010 (p. 46).

Altman, Andrew M. et al., IFATS Collection: Human Adipose-Derived Stem Cells Seeded on a Silk Fibroin-Chitosan Scaffold Enhance Wound Repair in a Murine Soft Tissue Injury Model. Stem Cells. 2009; 27: 250-258.

Bai, Lianhua et al., Hepatocyte growth factor mediates MSCs stimulated functional recovery in animal models of MS. National Institute of Health, Author Manuscript, Nat. Neurosci. 2012. pp. 862-870.

He, Hua et al., Biochemical Characterization and Function of Complexes Formed by Hyaluronan and the Heavy Chains of Inter-a-inhibitor (HC-HA) Purified from Extracts of Human Amniotic Membrane. Journal of Biologicial Chemistry 2009. vol. 284, No. 30.

Lee, Stuart S. et al., Bone regeneration with low dose BMP-2 amplified by biomimetic supramolecular nanofibers within collagen scaffolds. Biomaterials 34 (2013) 452-459.

Sierra, J. Rafael et al., c-MET as a potential therapeutic target and biomarker in cancer. Therapeutic Advances in Medical Oncology. 2011. S21-S35.

Wen, Qian et al., Change in hepatocyte growth factor concentration promote mesenchyman stem-mediated osteogenic regeneration. J. Cell. Mol. Med. vol. 16, No. 6. 2012. pp. 1260-1273.

Fries, Erik et al., Inter-a-inhibitor, hyaluronan and inflammation. Acta Biochinica Polonica. vol. 50 No. 3. 2003 pp. 735-742.

Rihn, Jeffrey A. et al., Graft Options in Posterolateral and Posterior Interbody Lumbar Fusion. SPINE vol. 35, No. 17, pp. 1629-1639. 2010.

Takebayashi, Toshiaki et al., Hepatocyte Growth Factor/Scatter Factor Modulates Cell Motility Proliferation, and Proteoglycan Synthesis of Chondrocytes. The Journal of Cell Biology, vol. 129, No. 5, 1995. pp. 1411-1419.

Hossain, M. et al., Hepatocyte growth factor (HGF) adsorption kinetics and enhancement of osteoblast differentiation of hydroxyapatite surfaces. Biomaterials 26 (2005) 2595-2602.

Ohkawara, Nana et al., Hepatocyte Growth Factor Fusion Protein Having Collagen-Binding Activity (CBD-HGF) Accelerates Re-endothelialization and Intimal Hyperplasia in Balloon-injured Rat Caratid Artery. Journal of Atherosclerosis and Thrombosis. vol. 14, 2007, No. 4, 185-191.

Wakitani, Shigeyuki et al., Hepatocyte growth factor facilitates cartilage repair. Acta Orthop Scand 1997; 68 (5): 474-480.

Beviglia, Lucia et al., HGF Induces FAK Activation and Integrin-Mediated Adhesion in MTLn3 Breast Carcinoma Cells. Int. J. Cancer: 83, 640-649. 1999.

Mack, Judith A. et al., Hoxb13 knockout adult skin exhibits high levels of hyaluronan and enhanced wound healing. The FASEB Journal. Article 10, 2003.

Burdick, Jason A. et al., Hyaluronic Acid Hydrogels for Biomedical Applications. Advanced Healthcare Materials 2011, 23, H41-H56.

Colen, Sascha et al., Hyaluronic Acid in the Treatment of Knee Osteoarthritis. Biodrugs 2012, 26(4): 257-268.

Wodewotzky, T.I. et al., In vitro cultivation of canine multipotent mesenchyman stromal cells on collagen membranes treated with hyaluronic acid for cell therapy and tissue regeneration. Brazilian Journal of Medical and Biological Research. 2012. vol. 45(12) 1157-1162.

Shay, Elizabeth et al., Inhibition of Angiogenesis by HC-HA, a Complex of Hyaluronan and the Heavy Chain of Inter-a-Inhibitor, Purified from Human Amniotic Membrane. Investigative Ophthalmology & Visual Science, vol. 52, No. 5, 2011.

Crevensten, Gwen et al., Intervertebral Disc Cell Therapy for Regeneration: Mesenchymal Stem Cell Implantation in Rat Intervertebral Discs. Annals of Biomedical Engineering, vol. 32, No. 3. 2004 pp. 430-434.

Rugg, Marilyn S. et al., Characterization of Complexes Formed between TSG-6 and Inter-a-inhibitor That Act as Intermediates in the Covalent Transfer of Heavy Chains onto Hyaluronan. The Journal of Biological Chemistry. 2005. vol. 280, No. 27, pp. 25674-25686.

Sanggaard, Kristian W. et al., The TSG-6/HC2-mediated Transfer is a Dynamic Process Shuffling Heaving Chains between Glycosaminoglycans. he Journal of Biological Chemistry. 2010. vol. 285, No. 29, pp. 21988-21993.

Posel, Claudia et al., Density Gradient Centrifugation Compromises Bone Marrow Mononuclear Cell Yield. PLOS One. vol. 1, Issue 12. 2012.

Sierpinski, Paulina et al., The use of keratin biomaterials derived from human hair for the promotion of rapid regeneration of peripheral nerves. Biomaterials 29 (2008). pp. 118-128.

Kitamura, Kazuya et al., Human Hepatocyte Growth Factor Promotes Functional Recovery in Primates after Spinal Cord Injury. PLOS ONE. vol. 6, Issue 11. 2011.

Stabile, Kathryne J. et al., An Acellular, Allograft-Derived Meniscus Scaffold in an Ovine Model. The Journal of Arthroscopic and Related Surgery, vol. 26, No. 7. 2010. pp. 936-948.

Oliveira, Serafim M. et al., An improved collagen scaffold for skeletal regeneration. Journal of Biomedical Materials Research Part A. 2009.

Zhao, Jing, et al., Recruitment of Endogenous Stem Cells for Tissue Repair. Macromolecular Bioscience, 2008, 8, 836-842.

Silini, Antonietta, et al., Soluble Factors of Amnion-Derived Cells in Treatment of Inflammatory and Fibrotic Pathologies. Current Stem Cell Search & Therapy, 2013, 8, 6-14.

Akamaru, Tomoyuki, et al., Simple Carrier Matrix Modifications Can Enhance Delivery of Recombinant Human Bone Morphogenetic Protein-2 for Posterolateral Spine Fusion. SPINE vol. 28, No. 5, pp. 429-424, 2003.

Kokkalis, Zinon T., et al., Assessment of Processed Porcine Extracellular Matrix as a Protective Barrier in a Rabbit Nerve Wrap Model, J Reconstr Microsurg 2011; 27:29-3.

Whitlock, Patrick W., et al., A Novel Process for Optimizing Musculoskeletal Allograft Tissue to Improve Safety, Ultrastructural Properties, and Cell Infiltration. J Bone Joint Surg Am., 2012; 94:1458-67.

Whitlock, Patrick, W., et al., A naturally derived, cytocompatible, and architecturally optimized scaffold for tendon and ligament regeneration. Biomaterials 28 (2007) 4321-4329.

Kawasaki, Toshiki, et al., The effect of timing in the administration of hepatocyte growth factor to modulate BMP-2 induced osteoblast differentiation. Biomaterials 31 (2010) 1191-1198.

Calderon, Laura, et al., Type II Collagen-Hyaluronan Hydrogel—A Step Toward a Scaffold for Intervertebral Disc Tissue Engineering. European Cells and Materials vol. 20 2010 (pp. 134-148).

Tay, Bobby K-B, et al., Use of a Collagen-Hydroxyapatite Matrix in Spinal Fusion: A Rabbit Model. Spine: Nov. 1, 1998, vol. 23, Issue 21, pp. 2276-2281.

Wolchok, Jeffrey C., et al., Using Growth Factor Conditioning to Modify the Properties of Human Cell Derived Extracellular Matrix. DOI 10.1002/btpr.1625; Published online Sep. 27, 2012 in Wiley Online Library (wileyonlinelibrary.com).

Wielenga, Vera J. M., Expression of c-Met and Heparan-Sulfate Proteoglycan Forms of CD44 in Colorectal Cancer. American Journal of Pathology, vol. 157, No. 5, Nov. 2000.

Zhang, Suzhen, et al., Constitutive Expression of Inter-a-inhibitor (Ial) Family Proteins and Tumor Necrosis Factor-stimulated Gene-6 (TSG-6) by Human Amniotic Membrane Epithelial and Stromal Cells Supporting Formation of the Heavy Chain-Hyaluronan (HC-HA) Complex. The Journal of Biological Chemistry, vol. 287, No. 15, pp. 12433-12444, 2012.

* cited by examiner

PREPARATIONS CONTAINING HEPATOCYTE GROWTH FACTOR AND HYALURONIC ACID AND METHODS OF MAKING AND USING SAME

RELATED APPLICATION

This application claims priority to U.S. Provisional Patent Application No. 61/790,075, filed on Mar. 15, 2013, and titled, "Preparations Containing Hepatocyte Growth Factor and Hyaluronic Acid and Methods of Making and Using Same," the entire contents of which are incorporated herein by reference.

FIELD OF THE INVENTION

The present invention is directed to preparations containing hepatocyte growth factor and hyaluronic acid and methods of making and using same.

BACKGROUND OF THE INVENTION

Hepatocyte growth factor (HGF) was first discovered as a protein that promotes the growth of rat hepatocytes in primary culture and was later cloned. HGF was also found to be a multifunctional factor that promotes proliferation, motility and morphogenesis in epithelial cells, and has since been found to have effects on stromal cells and multipotent cells from a number of other tissues, including cartilage. While HGF has been shown to have beneficial effects in several studies, the usefulness of HGF has been limited by several factors. First, the half-life of HGF in the body is extremely short, estimated at around five minutes. This precludes the effectiveness of a simple injection of the compound, or passive adsorption onto a dense surface for most purposes. (Hossain, M., et. al., Hepatocyte Growth Factor (HGF) Adsorption Kinetics and Enhancement of Osteoblast Differentiation on Hydroxyapatite Surfaces. *Biomaterials* (2005) 26:2595-2602). Second, the primary receptor of HGF, c-MET, is believed to be implicated in the invasiveness of some types of tumors, raising concerns about the safety of HGF in large doses. Some studies have suggested that HGF may discourage desirable cell differentiation, such as osteogenesis. This is believed to be a function of concentration. (Wen, Qian, Change in Hepatocyte Growth Factor Concentration Promote Mesenchymal Stem Cell-mediated Osteogenic Regeneration. *J. Cell. Mol. Med*. (2012) 16(2):1260-1273). Accordingly, it is desirable to provide a method for delivering HGF in low but effective doses specifically to the desired therapeutic site. Additionally, it may be desirable that the concentration of HGF diminish relatively rapidly over time. (Kawasaki, Tishiki, et. al., The Effect of Timing in the Administration of Hepatocyte Growth Factor to Modulate BMP-2-induced Osteoblast Differentiation. *Biomaterials* (2010) 31:1191-1198).

Hyaluronic acid (HA), or hyaluronan, is a linear polysaccharide that consists of alternating units of a repeating disaccharide, β-1,4-D-glucuronic acid-β-1,3-N-acetyl-D-glucosamine. HA is found throughout the body, from the vitreous of the eye to the extracellular matrix (ECM) of various tissues. HA is an essential component of the ECM, believed to be involved in cellular signaling, wound repair, morphogenesis, and matrix organization. Additionally, HA is rapidly turned over in the body by hyaluronidase, with half-lives ranging from hours to days. HA and its derivatives have been used clinically in a variety of applications. For example, HA in an injectable form is used routinely in ocular surgery, as a dermal filler, and in the treatment of arthritis of the synovial joints.

It has been shown that the addition of HGF to a semi-synthetic hydrogel containing HA chemically cross-linked with a number of other components allowed the continued delivery of HGF over several days. (Zhao, Jing, et al., Recruitment of Endogenous Stem Cells for Tissue Repair. *Macromol. Biosci*. (2008) 8:836-842). However, such hydrogels are chemically complex, contain synthetic materials, may be difficult for cells to remodel due to the extensive cross-linking with synthetic materials, and may retain HGF for too long a time. They may also be mechanically inappropriate for certain applications. For example, such hydrogels alone may be mechanically too weak for tissue repair applications. (Burdick, Jason A., et. al., Hyaluronic Acid Hydrogels for Biomedical Applications. *Adv. Mater*. (2011) 23:H41-H56). On the other hand, such gels may be too viscous and resistant to dispersion for use in an injectable therapy, such as in the synovial joints.

Therefore a need remains for preparations which will allow the beneficial delivery of HGF across a variety of surgical applications.

SUMMARY OF THE INVENTION

The present invention is directed to preparations containing hepatocyte growth factor and hyaluronic acid and methods of making and using same. In one embodiment, HGF and HA are prepared together in solution as an injectable fluid, without gelatinization. It is believed that the presence of HA alone will be sufficient to extend the delivery of HGF for clinically relevant time periods, and will allow physiological dispersion of the compounds. Such an injectable can be used for a variety of applications, including injection of the synovial joints for the treatment of chondral defects and degenerative conditions, as well as the enhancement of tissue repair methods such as Anterior Cruciate Ligament (ACL) repair, rotator cuff repair, and nerve repair.

In another embodiment, a porous hydrophilic matrix material is soaked in the fluid of the first embodiment, absorbing the fluid, prior to implantation. The matrix selected may have different material and mechanical properties depending on the surgical application. For example, the matrix may be composed of human or animal collagen (including, but not limited to, for example, type I collagen, type II collagen, and/or type IV collagen), hydroxyapatite, tri-calcium phosphate, cancellous bone, demineralized bone, processed human or animal soft tissues, processed human or animal nerves, or some combination thereof.

In another embodiment, HA is physically incorporated into and cross-linked in situ within a porous matrix, with limited or no chemical cross-linking of the HA with the material forming the matrix. This may be accomplished by a variety of means. In one approach, an existing matrix may be soaked with HA, with the addition of cross-linking heavy chains of inter-alpha inhibitor (IaI) along with the catalyst Tumor Necrosis Factor Stimulating Gene-6 (TSG-6), which physiologically and specifically cross-link HA molecules with one another. (Sanggard, Kristian W., et. al., The TSG-6/HC2-mediated Transfer is an Dynamic Process Shuffling Heavy Chains Between Glycosaminoglycans. *J. Biol. Chem*. (2010) 285:21988-21993; Rugg, Marilyn S., et. al., Characterization of Complexes Formed Between TSG-6 and Inter-α-Inhibitor that Act as Intermediates in the Covalent Transfer of Heavy Chains onto Hyaluronan. *J. Biol. Chem*. (2005) 280(27):25674-25686; Fries, Erik, et. al., Inter-α-Inhibitor, Hyaluronan and Inflammation. *Acta Biochem. Pol.* (2003) 50(3):735-742). If desired, HGF may be added to the mixture during the polymerization stage, or the final product may be soaked in a mixture containing HGF thereafter. Alternatively, cells which constitutively express HA, IaI, and TSG-6, such as amniotic-derived multipotent cells may be seeded and cultured in the matrix. (Zhang, Suzhen, et. al., Constitutive Expression of Inter-α-inhibitor (IαI) Family Proteins and Tumor Necrosis Factor-stimulated Gene-6 (TSG-6) by Human Amniotic Membrane Epithelial and Stromal Cells Supporting Formation of the heavy Chain-Hyaluronan (HC-HA) Complex. *J. Biol. Chem.* (2012) 287 (15):12433-12444). Exogenous HA may be added to the culture solution. If desired, HGF may also be added to the culture solution, as may other proteins which encourage the formation and deposition of HA by cells. Thereafter, the cells may be removed and the matrix sterilized using techniques well known in the art, such as irradiation.

In another embodiment, the invention is directed to a method of generating cartilage in vivo in a skeletal joint, the method including removing a diseased cartilage portion from a cartilage body of the skeletal joint, wherein the leakage of blood caused by removing the diseased cartilage portion is minimized, and essentially all of the blood from the skeletal joint is removed prior to implantation of a preparation into the skeletal joint. The diseased cartilage may be removed in a manner that leaves sustainably all of the healthy cartilage intact. To the extent possible, the diseased cartilage may be removed without disturbing the underlying calcified cartilage and bone. If removing the diseased cartilage portion exposes the underlying bone, the bone may be leaking blood, which, along with any blood clots, may be removed. A biodegradable, semi-permeable or impermeable membrane may be applied to cover the bleeding bony surface, following which a porous matrix containing HGF and HA may be applied to fill the void in the joint. The membrane may be incorporated with, or separate from, the matrix.

A further understanding of the nature and advantages of the present invention will be realized by reference to the remaining portions of the specification.

DETAILED DESCRIPTION OF THE INVENTION

Before the present compositions, articles, devices, and/or methods are disclosed and described, it is to be understood that they are not limited to specific methods unless otherwise specified, or to particular reagents unless otherwise specified, and as such may vary. It is also to be understood that the terminology as used herein is used only for the purpose of describing particular embodiments and is not intended to be limiting.

This application references various publications. The disclosures of these publications and other publications, which were submitted with U.S. Provisional Patent Application No. 61/790,075, in their entireties, are hereby incorporated by reference into this application to describe more fully the state of the art to which this application pertains.

A. Methods of Making Preparations

In one embodiment, HGF and HA are prepared together in solution as an injectable fluid, without gelatinization. It is believed that the presence of HA alone will be sufficient to extend the delivery of HGF for clinically relevant time periods, and the absence of gelatinization will allow dispersion of the compounds in physiologic fluids and within tissues. As is well known in the art, the HA chosen may be derived from various human or animal sources, and may be of various molecular weights, or a combination of molecular weights. (Colen, Sascha, et. al., Hyaluronic Acid in the Treatment of Knee Osteoarthritis. *Biodrugs* (2012) 26(4): 257-268). The HA may also be produced through recombinant technologies, for example by genetically modified bacteria. HGF may be derived from human or animal sources, may be synthesized, or may be produced using recombinant techniques or other techniques involving the genetic modification of bacteria or other cells. Additionally, related compounds which possess the biochemical activity of HGF may be used in its place. Such compounds and methods of their development are well known in the art. (Ohkawara, Nana, et. al., Hepatocyte Growth Factor Fusion Protein Having Collagen-Binding Activity (CBD-HGF) Accelerates Re-endothelialization and Intimal Hyperplasia in Balloon-injured Rat Carotid Artery. *J. Athero. Thromb.* (2007) 14:185-191; Ross, J., et. al., Protein engineered variants of hepatocyte growth factor/scatter factor promote proliferation of primary human hepatocytes and in rodent liver. *Gastroenterology.* (2012) 142(4):897-906).

In another embodiment, a porous hydrophilic matrix material is soaked in the fluid of the first embodiment, absorbing the fluid, prior to implantation. The matrix selected may have different material and mechanical properties depending on the surgical application. For example, the matrix may be composed of human or animal collagen, silk or silk proteins, hydroxyapatite, tri-calcium phosphate, cancellous bone, demineralized bone, processed human or animal soft tissues, processed human or animal nerves, or some combination thereof. A wide array of such matrices with different material properties are well known in the art. (See Oliveira, Serafim M., et al., An Improved Collagen Scaffold for Skeletal Regeneration. *J Biomed Mater Res Part A*, (2010) 94:372-376; Stabile, Kathryne J., et. al., An Acellular, Allograft-Derived Meniscus Scaffold in an Ovine Model. *Arthroscopy* (2010) 26:936-948; Rihn, Jeffrey A., et. al., Graft Options in Posterolateral and Posterior Interbody Lumbar Fusion. *Spine* (2010) 35(17):1629-1639; Altman, Andrew M., et. al., IFATS Collection: Human Adipose-Derived Stem Cells Seeded on a Silk Firboin-Chitosan Scaffold Enhance Wound Repair in a Murine Soft Tissue Injury Model. *Stem Cells* (2009) 27:250-258; Whitlock, Patrick W., et. al., A Novel Process for Optimizing Musculoskeletal Allograft Tissue to Improve Safety, Ultrastructural Properties, and Cell Infiltration. *J. Bone Joint Surg. Am.* (2012) 94:1458-1467; Tay, Bobby K-B, et. al., Use of a Collagen-Hydroxyapatite Matrix in Spinal Fusion: A Rabbit Model. *Spine* (1998) 3(21):2276-2281; and U.S. Pat. Nos. 4,544,516 and 5,399,351, the entire contents of which are incorporated herein by reference).

In another embodiment, HA is physically incorporated into and cross-linked in situ within a porous matrix, with limited or no chemical cross-linking of the HA with the material forming the matrix. This may be accomplished by a variety of means. In one approach, an existing matrix may be soaked with HA, with the addition of cross-linking heavy chains of inter-alpha inhibitor (IaI) along with the catalyst Tumor Necrosis Factor Stimulating Gene-6 (TSG-6), which physiologically and specifically cross-link HA molecules with one another (Sanggard, Kristian W., et. al., The TSG-6/HC2-mediated Transfer is an Dynamic Process Shuffling Heavy Chains Between Glycosaminoglycans. *J. Biol. Chem.* (2010) 285:21988-21993; Fries, Erik, et. al., Inter-α-Inhibitor, Hyaluronan and Inflammation. *Acta Biochem. Pol.* (2003) 50(3):735-742; Rugg, Marilyn S., et. al., Characterization of Complexes Formed Between TSG-6 and Inter-α-

Inhibitor that Act as Intermediates in the Covalent Transfer of Heavy Chains onto Hyaluronan. *J. Biol. Chem.* (2005) 280(27):25674-25686). As is known in the art, related compounds which possess the biochemical activity of the IaI heavy chains and TSG-6 may be used in their place. These compounds will catalyze the in situ cross-linking of HA with other HA molecules, with limited or no cross-linking with the existing matrix. If desired, HGF may be added to the mixture during the cross-linking stage, or the final product may be soaked in a solution containing HGF thereafter, allowing passive absorption of HGF. Alternatively, cells which constitutively express HA, IaI, and TSG-6, such as amniotic-derived multipotent cells (Zhang, Suzhen, et. al., Constitutive Expression of Inter-α-inhibitor (IαI) Family Proteins and Tumor Necrosis Factor-stimulated Gene-6 (TSG-6) by Human Amniotic Membrane Epithelial and Stromal Cells Supporting Formation of the heavy hain-Hyaluronan (HC-HA) Complex. *J. Biol. Chem.* (2012) 287 (15):12433-12444), may be seeded and cultured in the matrix, where they will deposit cross-linked HA. Exogenous HA may be added to the culture solution. If desired, HGF may also be added to the culture solution, as may other proteins which encourage the formation and deposition of HA by cells. The final product may also be soaked in a solution containing HGF, allowing passive absorption of HGF. Thereafter, the cells may be removed and the matrix sterilized using techniques well known in the art, such as irradiation.

Depending on the intended use, other growth factors and anti-inflammatory compounds may be included with HGF in the preparations. These may include but not be limited to Vascular Endothelial Growth Factor (VEGF), Insulin-Like Growth Factor (ILGF), basic Fibroblast Growth Factor (bFGF), Epidermal Growth Factor (EGF), Interleukin-10 (IL-10), and members of the Transforming Growth Factor-Beta subfamily, including TGF-β1, TGF-β3, and the bone and cartilage morphogenetic proteins.

Similarly, multipotential cells from various sources, including amniotic, bone-marrow derived, adipose-derived, synovium-derived, blood derived, and induced pluripotent cells may be incorporated into the embodiments. Such cells may be autologous or from human or animal sources. They may be cultured, for example in solution for injection or after seeding onto a matrix embodiment, or uncultured.

B. Uses of the Preparations

The embodiments of the preparation, described herein, may be used to regenerate damaged or defective tissue.

1. Synovial Joint Degeneration and Cartilage Defects.

An injectable embodiment can be used for a variety of applications, including injection of the synovial joints for the treatment of chondral defects and degenerative conditions of the synovial joints. Synovial joints are subject to degeneration from arthritis and other conditions, resulting in painful inflammation and ultimately disruption of the cartilaginous linings of the joint.

Furthermore, substantial defects in the articular cartilage may develop due to degenerative conditions, trauma, or other pathologies. Articular cartilage, located on the articular ends of bones at joints throughout the body, is composed of hyaline cartilage and contains relatively few chondrocytes that are embedded in extracellular matrix materials, such as type II collagen and proteoglycan (Moriya T, et al., Evaluation of reparative cartilage after autologous chondrocyte implantation for osteochondritis dissecans: histology, biochemistry, and MR imaging. *J Orthop Sci* (2007) 12:265-273). Articular cartilage has a limited ability to self-repair, in part due to the avascular characteristics of the cartilage, which poses a significant challenge to treating joint injuries or diseases. The repair of cartilage defects in humans can therefore be a difficult endeavor, and multiple options exist for the surgeon to approach this topic. The surgeon may choose to influence the defect with microfracture or abrasion techniques to stimulate bleeding and a resulting fibrocartilage patch with which to fill the defect. There are also options available that allow for the filling of the defect with chondrocytes of variable sources, both of autograft and allograft origin. However, current treatments, including cell-based therapies, have resulted in the generation of undesirable fibrocartilaginous tissue rather than hyaline cartilage (Diaz-Prado S M, et. al. BIOMEDICAL ENGINEERING, TRENDS, RESEARCH, AND TECHNOLOGIES, pp. 193-216 (2011)). As such, there remains a significant clinical need for therapies capable of repairing damaged articular cartilage that are capable of regenerating hyaline cartilage.

It is well known in the art to inject HA into joints to reduce the pain and inflammation resulting from degenerative joint conditions. Furthermore, at least one study has established the beneficial effect of the injection of HGF alone for the treatment of a cartilage defect in an animal model. (Wakitani, Shigeyuki, et. al., Hepatocyte Growth Factor Facilitates Cartilage Repair. *Acta Orthop Scand* (1997) 68(5):474-480). However the treatment protocol involved multiple times per week over four weeks, likely due to the short half-life of HGF. Such a protocol for multiple joint injections is not clinically or economically feasible for use in human patients. The method of the invention, which permits the combination of HGF with HA, which among other effects should slow HGF degradation as well as reducing pain and inflammation, should dramatically reduce the number of required injections and improve the efficacy of treatment.

For larger cartilage defects, the injectable embodiment may be insufficient, and treatment may require the placement of an appropriate matrix for tissue in-growth, which may be either soaked in an injectable HA/HGF preparation, or may contain cross-linked HA as more particularly described above. Preferably, the matrix in question may be a human or bovine collagen product, either formed in the laboratory from dissolved collagen or created by the processing of tissues such as demineralized bone. During the removal of diseased cartilage prior to implantation of the matrix, the subchondral bone may inadvertently be perforated or abrasions formed. Perforations or abrasions in the subchondral bone or the calcified cartilage may induce bleeding and the formation of a fibrous clot in the defect, as well as the subsequent invasion of mesenchymal progenitor cells from the bone marrow to the site of the damaged cartilage. For this reason, cartilage repair procedures currently in use such as microfracture intentionally perforate the subchondral bone in order to induce clotting and initiate repair. However, introduction of blood and/or mesenchymal progenitor cells from the bone marrow into the void may induce the formation of fibrocartilage in place of the desired hyaline cartilage. Accordingly, in the claimed method the leakage of blood should be minimized, and any blood clots that may form as a result of the blood leakage should be removed. Techniques for the removal of blood and blood clots are well-known to those skilled in the art. Such techniques may include, but are not limited to, for example, aspiration. Hemostatic agents including, but not limited to, bone wax may also be applied to the site of blood leakage, typically exposed subchondral bone. Bone marrow may also be released from the subchondral bone, during or proximal to the implantation of the placental membrane preparation.

The bone marrow may be removed using techniques well-known to those skilled in the art. Techniques include, but are not limited to, aspiration.

To further slow the invasion of cells from the marrow, a biodegradable, semi-permeable or impermeable membrane may be applied to cover the bleeding bony surface of the joint prior to placement of the matrix. In this way, blood that may collect within a void formed in a joint is separated or shielded from the interior of the matrix where chondrogenic growth and differentiation occurs in contact with cartilage on the lateral sides of the graft. By preventing the leakage of blood into the matrix, it is believed the mechanisms which cause fibrocartilage and osteoblast formation are substantially reduced or terminated. The membrane may be incorporated with, or separate from, the matrix. It may be synthetic or derived from human or animal membranes, such as human amnion.

Defects in or injuries to the meniscus of the knee may be treated in a similar fashion.

2. Ligament and Tendon Repair.

Due to trauma, overuse, and for other reasons, ligaments and tendons in the body may fully or partially tear, requiring surgical repair. Common examples include repair of the cruciate and medial collateral ligaments in the knee, the Achilles tendon, and the rotator cuff of the shoulder and hip. While numerous surgical techniques are available for conducting these repairs, in many cases the repairs fail to heal as rapidly and as fully as desired. The healing of rotator cuff repairs is particularly challenging. Additionally, even in the absence of large tears, tendons, ligaments and other connective tissues may become damaged and inflamed, resulting in painful and debilitating conditions. The disclosed embodiments may be effectively used in the treatment of such conditions.

The injectable embodiment may be used to treat tendon, ligament and connective tissue inflammation by direct injection of the affected area. During surgical ligament and tendon repairs, the grafting materials may be soaked in or injected with the injectable embodiment. Alternatively, the repair site may be injected with the injectable embodiment. Even using HGF alone, such injections have been shown to be beneficial in improving outcomes. (Nakase, J., et. al., Facilitated Tendon-bone Healing by Local Delivery of Recombinant Hepatocyte Growth Factor in Rabbits. *Arthroscopy* (2010) 26(1):84-90). A matrix according to the invention may be incorporated into the repair site via sutures or surgical glue during the surgery itself, in order to encourage healing between the grafted materials and the surrounding tissue. Similarly, one or more injections into the joint capsule or at the repair site following a reparative surgery should be beneficial in speeding graft incorporation and healing.

3. Peripheral Nerve Repair.

The management of trauma-associated nerve defects is difficult. While nerve autograft is the gold standard, there are limited sources of motor and sensory nerves and grafting inevitably results in a nerve deficit at the donor site. Prior research has shown that damaged nerves can be surgically repaired using a tubular conduit crossing the defect, and processed allograft nerves have also been successfully used for this purpose. However, healing is slow and particularly for larger nerve gaps often results in less than satisfactory recovery of function. Accordingly it has been suggested that the inclusion on an appropriate biomaterial within the tubular conduit may improve functional outcomes. (Sierpinski, Paulina, et al., The Use of Keratin Biomaterials Derived from Human Hair for the Promotion of Rapid Regeneration of Peripheral Nerves. *Biomaterials* (2008) 29:118-128). Similarly, the addition of neurotrophic factors to a processed human or animal nerve may enhance the performance of the nerve graft. In animal models of spinal cord injury, HGF has been shown to be beneficial to nerve growth and repair (Kitamura, Kazuya, et. al., Human Hepatocyte Growth Factor Promotes Functional Recovery in Primates After Spinal Cord Injury. *PloS ONE* (2011) 6(11):e277706). The disclosed embodiments may be effectively used for such purposes.

Specifically, in surgery for which a conduit is used, the injectable embodiment may be incorporated to fill the conduit during the repair surgery. The conduit itself, or a highly porous filler material, may be soaked in the injectable embodiment. Alternatively, a highly porous matrix embodiment may be placed inside the nerve conduit prior to implantation. In surgery for which a processed nerve is to be used, the nerve may itself be used as a matrix for addition of HA and HGF, using any of the methods described herein.

4. Spinal Disc Degeneration.

Intervertebral discs are fibrocartilaginous tissues occupying the space between vertebral bodies in the spine. They transmit forces from one vertebra to the next, while allowing spinal mobility. The structural properties of the disc are largely depending on its ability to attract and retain water. Proteoglycans in the disc exert an osmotic "swelling pressure" that resists compressive loads. Degeneration of the intervertebral disc is a physiologic process that is characteristic of aging in humans. With age, the disc undergoes a variety of changes, the most notable being a loss of proteoglycan content resulting in reduced osmotic pressure and a reduction in disc height and ability to transmit loads. Disc degeneration is an important and direct cause of spinal conditions that account for most neck and back pain.

As is the case with the related cartilage and tendon cells, HGF is believed to promote healing and recovery of the intervertebral disc and associated cells. Various disc treatment compositions incorporating HA have also been the subject of pre-clinical experimentation. (Park, S. H., et. al., Intervertebral Disk Tissue Engineering Using Biphasic Silk Composite Scaffolds. *Tissue Eng. Part A*, (2012) 18(5-6): 447-458). Accordingly, it is believed that the disclosed invention may be beneficially used in the treatment of degenerative disc disease. Specifically, the injectable embodiment may be injected into the disc. The injection may be combined with, or followed by, the injection of a fibrin sealant or other adhesive matrix to seal the hole in the disc created by the injection. (Buser Z, et. al., Biological and Biomechanical Effects of Fibrin Injection into Porcine Intervertebral Discs. Spine (2011) 36(18)1201-1209).

5. Wound and Burn Care.

The treatment of large-scale burns and non-healing wounds is extremely challenging. Though many treatment options are available, some wounds are recalcitrant to treatment, and many do not heal with satisfactory results. Both HGF and HA are believed to play important roles in dermal healing. (Mack, Judith A., et. al., Hoxb13 Knockout Adult Skin Exhibits High Levels of Hyaluronan and Enhanced Wound Healing. *FASEB J.* (2003) 10.1096/fj.02-0959fje; Honda, K., et. al., A novel mechanism in maggot debridement therapy: protease in excretion/secretion promotes hepatocyte growth factor production. *Am J Physiol Cell Physiol.* (2011) 301(6):C1423-30). Accordingly, it is believed that the disclosed invention may be beneficially used in the treatment of non-healing wounds and burns.

Specifically, the injectable embodiment may be injected around or in the wound bed, stimulating healing. Matrices according to the other embodiments may be placed directly onto the healing wound or burn. Preferably, such matrices would have a thickness approximating that of human skin.

6. Bone Growth and Fusion.

At appropriate concentrations, HGF has been shown to promote bone growth. In some applications, such as the treatment of non-healing fractures of the long bones, or the treatment of a scaphoid non-union, it may be desirable to inject a substance to enhance bone healing. An injectable embodiment may effectively be used in such applications. Alternatively, for applications that require or permit grafting to fill a bony void, hydrophilic graft material may be soaked in an injectable embodiment prior to use, or a matrix embodiment may be used. The graft material used may be autograft, allograft, xenograft, or synthetic, or some combination thereof.

7. Dermal Filler.

There are numerous cosmetic and plastic surgery applications in which dermal fillers may be used to restore the appearance of the skin. It is often desirable that the products used be injectable, but sufficiently viscous to remain in place after injection. The products may also be placed surgically, through catheters, or via various other means known in the art. Numerous products have been investigated or used clinically. (Kontis, Theda C., Contemporary Review of Injectable Facial Fillers. *Facial Plast. Surg.* (2013) 15(1): 58-64). Various formulations of hyaluronic acid are widely used for this purpose. HGF has been shown to support the healing of the skin and connective tissue. The injectable embodiment, with or without the addition of other biocompatible materials, such as, for example, collagen, fibrin or keratin, may be appropriately used as an injectable dermal filler. A loose matrix may also be soaked in the injectable embodiment, and implanted beneath the skin as a dermal filler.

What is claimed is:

1. A method of regenerating damaged or defective tissue comprising:
   making a preparation by cross-linking hyaluronic acid (HA) in situ within a porous matrix, with limited or no chemical cross-linking of the hyaluronic acid with a material forming the porous matrix, by soaking the porous matrix with the hyaluronic acid, with the addition of cross-linking heavy chains of inter-alpha inhibitor and Tumor Necrosis Factor Stimulating Gene-6, wherein hepatocyte growth factor (HGF) is added to the preparation during the HA cross-linking stage or the HGF is added after the HA cross-linking stage by soaking the preparation in a solution containing HGF, and placing the preparation containing HGF into a synovial joint of the mammal.

2. The method according to claim 1 wherein the synovial joint includes a chondral defect.

3. The method according to claim 1 wherein the synovial joint includes a meniscal defect.

4. The method according to claim 1 wherein the synovial joint presents with osteoarthritis.

5. The method according to claim 1 wherein placing the preparation into the synovial joint promotes hyaline cartilage regeneration in the synovial joint.

6. The method according to claim 1 wherein the presence of HA in the preparation slows a rate of HGF degradation in the preparation.

7. The method according to claim 1 wherein the presence of HA in the preparation slows a rate of HGF degradation in vivo.

8. The method according to claim 1 where the HA is produced using a recombinant system involving genetic modification of bacteria.

9. The method according to claim 1 further comprising excluding gelatin from the preparation.

10. The method according to claim 1 further comprising excluding a synthetic polymer from the preparation.

11. A composition made by
   a) making a preparation by cross-linking hyaluronic acid (HA) in situ within a porous matrix, with limited or no chemical cross-linking of the hyaluronic acid with a material forming the porous matrix, by soaking the porous matrix with the hyaluronic acid, with the addition of cross-linking heavy chains of inter-alpha inhibitor and Tumor Necrosis Factor Stimulating Gene-6, and
   b) adding hepatocyte growth factor (HGF) to the preparation of a) during the HA cross-linking stage or adding HGF after the HA cross-linking stage by soaking the preparation in a solution containing HGF.

12. A method of promoting healing of a diseased or damaged tissue of a mammal comprising:
   making a preparation by cross-linking hyaluronic acid (HA) in situ within a porous matrix, with limited or no chemical cross-linking of the hyaluronic acid with a material forming the porous matrix, by soaking the porous matrix with the hyaluronic acid, with the addition of cross-linking heavy chains of inter-alpha inhibitor and Tumor Necrosis Factor Stimulating Gene-6, wherein hepatocyte growth factor (HGF) is added to the preparation during the HA cross-linking stage or the HGF is added after the HA cross-linking stage by soaking the preparation in a solution containing HGF, and applying the preparation to a diseased or damaged tissue selected from the group consisting of cartilage tissue, nerve tissue, bone tissue, vertebral disc tissue, muscle tissue, and connective tissue, where the amount of HA is sufficient to decrease the rate of degradation of the HGF in the preparation and in vivo.

13. The method according to claim 12 further comprising selecting the porous matrix from the group consisting of collagen, hydroxyapatite, tri-calcium phosphate, cancellous bone, demineralized bone, processed human or animal soft tissues, processed human or animal nerves, and combinations thereof.

* * * * *